United States Patent [19]

Kaplan et al.

[11] 4,161,595

[45] Jul. 17, 1979

[54] LEVULINIC ACID SALT

[75] Inventors: Murray A. Kaplan, Syracuse; Alphonse P. Granatek, Baldwinsville, both of N.Y.

[73] Assignee: Bristol-Myers Company, New York, N.Y.

[21] Appl. No.: 947,678

[22] Filed: Oct. 2, 1978

[51] Int. Cl.² ............................................. C07D 239/95
[52] U.S. Cl. ...................................... 544/284; 424/251
[58] Field of Search .......................................... 544/284

[56] References Cited

U.S. PATENT DOCUMENTS 4,001,238  1/1977  Partyka et al. ................. 260/256.4 B Primary Examiner—Raymond V. Rush
Attorney, Agent, or Firm—Robert H. Uloth

[57] ABSTRACT

The invention concerns a levulinic acid addition salt of the antihypertensive agent 4-amino-6,7-dimethoxy-2-[4-(5-methylthio-1,3,4-oxadiazole-2-carbonyl]piperazin-1-yl)quinazoline in which the base to acid mole ratio is 1 to from 1.25–1.35. The salt is characterized in having improved water solubility and stability compared to the levulinate salt having a 1:1 ratio of base to acid.

2 Claims, No Drawings

LEVULINIC ACID SALT

BACKGROUND OF THE INVENTION

This invention deals with a drug, bio-affecting and body-treating type of compound. More specifically, this invention is concerned with the levulinic acid addition salt of 4-amino-6,7-dimethoxy-2-[4-(5-methylthio-1,3,4-oxadiazole-2-carbonyl]piperazin-1-yl)quinazoline containing a base to acid ratio of 1 to from 1.25–1.35. The free base form of the instant compound is also referred to herein by code number BL-5111 and is represented by the following structural formula.

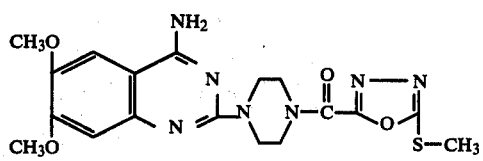

Partyka, et al., U.S. Pat. No. 4,001,238 describe preparation of BL-5111 and its use as an antihypertensive agent. As stated therein, BL-5111 may be used for antihypertensive purposes as the free base or in the form of pharmaceutically acceptable acid salts thereof. Specifically, U.S. Pat. No. 4,001,238 at column 10, lines 12–13, discloses that salts of sulphuric acid, hydrochloric acid, succinic acid, tartaric acid, and benzoic acid are operable.

When a substance is employed for medical purposes, it is recognized that solubility of the therapeutic agent often is the controlling factor in determining route of administration and dosage forms. For instance, a water-soluble substance can be generally administered intravenously whereas a water-insoluble material is limited to other forms of parenteral administration such as intramuscular and subcutaneous. Since most parenteral products are preferably prepared as solutions, a therapeutic agent having water solubility likewise facilitates preparation of oral and various parenteral dosage forms for human administration. Thus, it is decidedly advantageous if a therapeutic agent is water-soluble and suited for parenteral administration particularly when one considers that the most direct route for achieving therapeutic blood levels of a drug within the human body is by intravenous administration.

Accordingly, the primary object of the present invention is to provide a water-soluble, stable, therapeutically acceptable form of the antihypertensive agent BL-5111 which can be administered both orally and intravenously as well as by other parenteral routes. This object as well as other features and advantages of the invention will be readily apparent to those skilled in the art from the disclosure set out below and accompanying claims.

SUMMARY OF THE INVENTION

This invention is concerned with the levulinic acid addition salt of BL-5111 and in particular with the salt form in which the base to acid ratio comprises one mole equivalent of BL-5111 base to from 1.25 to 1.35 mole equivalent of levulinic acid.

Many conventional pharmaceutically acceptable acid addition salts of BL-5111 are only slightly soluble in water and thus are not suited for intravenous administration. This is clearly evident from the following table wherein relative solubility of various salts of BL-5111 including such specifically disclosed salts of U.S. Pat. No. 4,001,238 as the sulfuric, hydrochloric, succinic and tartaric acid salts is given. Solubility at room temperature (about 25° C.) and at 50° C. was determined in situ by stirring 10 mg. of BL-5111 free base in 0.3 ml. of water with an excess of the acid.

TABLE 1

| | Solubility of Acid Addition Salts of BL-5111 at 25° C. and 50° C. | |
|---|---|---|
| | Solubility[a] | |
| Acid | 25° C. | 50° C. |
| acetic | + | + |
| formic | ± | + |
| sulfuric | − | − |
| citric | − | − |
| pyruvic | ± | + |
| phosphoric | − | − |
| methanesulfonic | − | − |
| fumaric | − | − |
| tartaric | − | − |
| succinic | − | + |
| maleic | − | − |
| hydrochloric | − | − |
| nitric | − | − |
| lactic | + | + |
| hydrobromic | − | − |
| isethionic | − | − |
| levulinic | + | + |

[a] soluble (+) insoluble (−) questionable (±)

As seen in the above table, only the acetate, lactate and levulinate salts are sufficiently soluble at room temperature to provide a 3.3% (i.e. 10 mg./0.3 ml.) solution.

Preparation of the levulinic acid salt of BL-5111 as a solid is carried out by two methods. The first and preferred method comprises reacting BL-5111 free base with 1.3 mole equivalents of levulinic acid in a halogenated hydrocarbon solvent such as methylene chloride. Removal of the solvent by evaporation provides BL-5111 levulinate having a base to acid mole ratio of 1:1.3. An aqueous solution of this salt is stable at room temperature. In a similar fashion, the levulinate salt of BL-5111 containing a base to acid ratio of 1:1 can be obtained by reacting equimolar equivalents of BL-5111 and levulinic acid. However, as indicated by TABLE 2 data below, this salt is not particularly suited for purposes of the present invention inasmuch as it is relatively less soluble and stable than the 1:1.3 levulinate.

The second method comprises treating BL-5111 free base suspended in a halogenated hydrocarbon solvent, preferably methylene chloride, with excess levulinic acid to provide a solution of the BL-5111 levulinate salt. The levulinic acid is preferably employed in from 4 to 9 molar equivalents and most preferably from 5 to 7 molar equivalents. Addition of the acidified solution to ether precipitates the levulinate acid salt of BL-5111 as a crystalline solid containing a base to acid ratio equivalent to 1 mole of BL-5111 and from about 1.25 to 1.35 moles of levulinic acid. The salt obtained in this manner may be hydrated to the extent of from about 0.5 to 4% water.

Water stability and solubility comparisons of the 1:1 and 1:1.3 BL-5111 levulinate salts are given in the following table.

TABLE 2

| Comparative Water Solubility and Stability of 1:1 and 1:1.3 Levulinate Salts | | |
|---|---|---|
| Salt Form (Concentration) | Solubility | Stability |
| 1:1.3 (50 mg./ml.) | soluble at 50° C. | stable* |

TABLE 2-continued

Comparative Water Solubility and
Stability of 1:1 and 1:1.3 Levulinate Salts

| Salt Form (Concentration) | Solubility | Stability |
|---|---|---|
| 1:1.3 (10 mg./ml.) | soluble* | stable* |
| 1:1 (50 mg./ml.) | insoluble at 80° C. | free base separates |
| 1:1 (10 mg./ml.) | soluble at 50° C. | free base separates* |
| 1:1 (2.5 mg./ml.) | soluble at 50° C. | free base separates* |

*Room temperature

In comparison to the hydrochloride salt of BL-5111, the 1:1.3 levulinate salt form has substantially greater water and lipid solubility. TABLE 3 below sets forth results of a comparative quantitative study of the BL-5111 hydrochloride and the 1:1.3 levulinate salt in water and methylene chloride. Solubility in methylene chloride is a measure of lipid solubility which plays an important role in any distribution in the body.

TABLE 3

Solubility of the 1:1.3 Levulinate and Hydrochloride
Salt of BL-5111 in Water and Methylene Chloride at 25° C.

| BL-5111 Salt | Water mg./ml. | Methylene Chloride mg./ml. |
|---|---|---|
| 1:1.3 levulinate | 38.0 | >100 |
| hydrochloride | 4.42 | <1 |

Thus, it can be seen that the water solubility of BL-5111 levulinate salt is about 8.6 times that of the hydrochloride salt while methylene chloride solubility is increased by a factor of more than 100. As previously stated, water solubility constitutes a requirement for intravenous administration of a substance employed for medical purposes. Furthermore, practicality requires that the medicament have sufficient solubility to permit administration of an effective dose in a relatively small volume of parenteral solution.

With respect to oral administration, the BL-5111 levulinate provides improved absorption compared to the hydrochloride salt as illustrated by enhanced plasma levels in dogs. Thus, BL-5111 levulinate (equivalent to 10 mg. of BL-5111 free base) was orally administered by gavage as a solution in 5 ml. of water followed by 20 ml. of water to beagle dogs which had been fasted 12 to 15 hours. The BL-5111 hydrochloride (equivalent to 10 mg. of the BL-5111 free base) was likewise administered with the exception that a suspension was employed due to tendency of the hydrochloride to dissolve at a rate appreciably slower than the levulinate. It was found that the rate of absorption after administration of the levulinate was unexpectedly faster with maximum plasma levels reached within 0.75 to 1.0 hr. versus 2 hr. for the BL-5111 hydrochloride. Moreover, maximum plasma level following administration was approximately three-fold greater for the levulinate than the hydrochloride while the extent of absorption of BL-5111 levulinate (determined by comparison of the area under plasma concentration-time curves taken over a period of 24 hr.) was more than double that of BL-5111 hydrochloride.

The instant water soluble levulinate salt can be intravenously administered to provide an effective antihypertensive amount of BL-5111. To some extent, the dose will vary depending upon the sensitivity of the patient to the drug and severity of the hypertension but generally an effective intravenous antihypertensive dose comprises from 0.5 to 5 mg. of BL-5111 levulinate 1:1.3 salt. In addition to intravenous administration, the instant levulinate salt may be administered as an antihypertensive agent by other parenteral routes such as intramuscular, subcutaneous, etc., as well as orally. A preferred oral unit dose comprises an enteric coated tablet of the BL-5111 levulinate (1:1.3) salt sufficient to provide from 5 to 15 mg. of BL-5111 as the active ingredient.

The following non-limiting examples illustrate the invention.

EXAMPLE 1

4-AMINO-6,7-DIMETHOXY-2-[4-(5-METHYLTHIO-1,3,4-OXADIAZOLE-2-CARBONYL)-PIPERAZIN-1-YL]QUINAZOLINE LEVULINATE (BL-5111 LEVULINATE 1:1.3)

Isolation of BL-5111 Free Base

Rapid addition of 10 ml. of 1 N sodium hydroxide to a suspension of BL-5111 hydrochloride (5.0 g.) in 50 ml. of rapidly stirred 95% ethanol provides a solution from which the free base begins to precipitate shortly after completing the addition (about 1 min.). The mixture is stirred for a period of 20 min. and the crystalline precipitate collected, washed with water, dried for a period of 24 hr. at 56° C. under high vacuum to afford 4-amino-6,7-dimethoxy-2-[4-(5-methylthio-1,3,4-oxadiazole-2-carbonyl)-piperazin-1-yl]quinazoline (BL-5111) free base, m.p. 228°–230° C.

Anal. Calcd. for $C_{18}H_{21}N_7O_4S$: C, 50.11; H, 4.91; N, 22.73. Found: C, 49.91; H, 4.94; N, 23.31.

This material can be used directly in preparation of the BL-5111 levulinate or crystallized from acetonitrile to provide material melting at 231°–233° C.

Preparation of BL-5111 Levulinate (1:1.3)

Method A

Levulinic acid (58.9 g., 0.507 mole) in 1 liter of dichloromethane poured into a vigorously stirred suspension of 4-amino-6,7-dimethoxy-2-[4-(5-methylthio-1,3,4-oxydiazole-2-carbonyl)-piperazin-1-yl]quinazoline (168.4 g, 0.39 mole) in 4 liters of dichloromethane provides a clear, lemon-yellow solution. The solution is stirred for approximately 0.5 hr., filtered, and the filtrate concentrated under reduced pressure (about 1 mm Hg.) to afford a bright yellow, friable solid froth. The frothy product is collected, pulverized, and dried to a constant weight at a reduced pressure of about 1 mm Hg over silica gel desiccant at room temperature to provide 228.7 g. (representing a yield of 100% when corrected for 0.68% water content) of the levulinic acid salt of 4-amino-6,7-dimethoxy-2-[4-(5-methylthio-1,3,4-oxadiazole-2-carbonyl)piperazin-1-yl]quinazoline.

Anal. Calcd. for $C_{18}H_{21}N_7O_4S.1.3C_5H_8O_3$: C, 50.52; H, 5.43; N, 16.84; S, 5.50. Found (corrected for 0.68% $H_2O$): C, 50.13; H, 5.16; N, 16.67; S, 5.55.

The 60 MHz nuclear magnetic resonance (NMR) spectrum measured in trifluoroacetic acid with tetramethylsilene as reference indicates the salt has a base to acid ratio of 1:1.3 with the following characteristics.

TABLE 4

60 MHz NMR Characteristics of BL-5111 . 1.3 Levulinic Acid Salt

| Chemical Shift (ppm) | Multiplicity | Relative Area (No. of H) | Structural Feature |
|---|---|---|---|
| 7.1 | s | 1 | H—⌬—H (aromatic ring with CH₃O groups) |
| 6.6 | s | 1 | |
| 3.7–4.1 | m | 14 total | —N(CH₂—CH₂)₂N— |
| 3.65 | s | | (CH₃O)₂ |
| 2.3–2.8 | m | 8.3 total | —CH₂—CH₂—C(=O)— |
| 2.4 | s | | CH₃—S |
| 1.95 | s | 4 | CH₃—C(=O) |

The infra spectrum (0.5% concentration in KBR) has the following absorption maxima: 505, 570, 635, 685, 751, 769, 785, 835, 985, 1005, 1020, 1085, 1110, 1155, 1210, 1240, 1260, 1285, 1380, 1395, 1435, 1465, 1485, 1525, 1555, 1595, 1650, 1710, 2935, 3230, 3350 cm$^{-1}$.

Method B

Levulinic acid (6.87 g., 59.15 mmoles) is added to 10 g. of BL-5111 free base (10 g., 23.18 mmoles) suspended in 50 ml. of methylene chloride. After stirring for a period of 15 min. the mixture is filtered and the filtrate added with rapid stirring over a period of 5 min. to 600 ml. of ether containing 9 ml. (10.3 g., 88.72 mmoles) of levulinic acid. Stirring is continued for a period of 5 min., and the crystals which form are then collected, washed with ether and dried under high vacuum for 24 hr. at 50°–56° C. to provide 12 g. of hydrated BL-5111 levulinate salt. According to 100 MHz NMR analysis this material is free from solvents and contains the equivalent of 1 mole of BL-5111 to 1.3 mole of levulinic acid.

Anal. Calcd. for $C_{18}H_{21}N_7O_4S \cdot 1.3 C_5H_8O_3$: C, 50.52; H, 5.43; N, 16.84; S, 5.50. Found (corrected for 2.4% water): C, 50.77; H, 5.69; N, 16.60; S, 5.35.

EXAMPLE 2

Preparation of BL-5111 (Levulinate (1:1)

Reaction of BL-5111 free base (10.0 g., 23.18 mmoles) with levulinic acid (2.69 g., 23.18 mmoles) according to the procedure of Example 1 (Method A) provides 10.0 g. of the levulinic acid salt of 4-amino-6,7-dimethoxy-2-[4-(5-methylthio-1,3,4-oxadiazole-2-carbonyl)-piperazin-1-yl]quinazoline. According to 100 MHz NMR analysis, the salt has a base to acid ratio of 1:1.

Anal. Calcd. for $C_{18}H_{21}N_7O_4S \cdot C_5H_8O_3$: C, 50.45; H, 5.34; N, 17.91; S, 5.85. Found (corrected for 0.86% $H_2O$): C, 50.36; H, 5.24; N, 17.97; S, 6.05.

Treating BL-5111 with a molar equivalent of levulinic acid in methylene chloride according to the procedure of Example 1 (Method B) provides a solid product which according to 100 MHz NMR analysis consists of 95% of the unreacted BL-5111 free base.

EXAMPLE 3

Solution For Parenteral Injection

A sterile solution of BL-5111 levulinate (1:1.3) suitable for intravenous injection is prepared by dissolving 27 g. of BL-5111 levulinate (1:1.3) in 1 liter of water for injection, USP. The solution is sterilized by passage through a bacteriological filter and stored in asceptically filled glass ampules. Calculated on a potency value of 74.0% base content each ml. of solution provides 20 mg. of the active ingredient.

EXAMPLE 4

Tablet for Oral Administration

The BL-5111 levulinate (1:1.3) salt of the instant invention is preferably administered as enteric-coated dosage forms which are formulated to release the BL-5111 levulinate content upon exposure to the mildly acetic fluids of the duodenum and to prevent drug release in the stomach. A Typical and operable film coated dosage form containing 10 mg. of BL-5111 as the active ingredient is a tablet having the following composition.

| Ingredient | Per Tablet, mg. |
|---|---|
| BL-5111 levulinate (1:1.3 ratio) | 13.498 |
| Lactose Anhydrous | 75.0 |
| Microcrystalline Cellulose (for wet granulation) | 79.002 |
| Starch, U.S.P. | 43.75 |
| Explotab Ⓒ (Sodium Starch Glycolate) | 12.5 |
| *Pluronic F-68 Ⓒ (Wyandote Corp.) | 12.5 |
| Microcrystalline Cellulose (for dry granulation) | 12.5 |
| Magnesium Stearate, U.S.P. (for dry granulation) | 12.5 |
| Net Weight Per Tablet | 250 |

*Contains 80% by weight of polyoxyethylene and 20% by weight of polyoxypropylene.

Tablets are prepared employing proportional amounts of the above ingredients as follows. A blend of anhydrous lactose, microcrystalline cellulose (for wet granulation), starch and Explotab Ⓡ is prepared. Approximately one-half the volume of a solution prepared by dissolving BL-5111 levulinate in a solution of Pluronic Ⓡ F-68 in sterile water (using a ratio of 1 mg.:0.12 ml. water) is added to the blend. The resulting mixture is granulated, dried and mixed with the remaining one-half volume of the BL-5111 levulinate solution, granulated and dried. The dried granulation is blended with microcrystalline cellulose (for dry granulation) and magnesium stearate, compressed to 250 g. tablets and film coated with a film coating solution having the following composition.

| Ingredient | Per Liter | |
|---|---|---|
| Hydroxypropyl Methylcellulose phthalate (Biddle-Sawyer) HB-50 | 40.0 | gm. |
| Ethyl alcohol, U.S.P. | 400.0 | ml. |
| Methylene chloride | 580.0 | ml. |

What is claimed is:

1. A levulinic acid addition salt of 4-amino-6,7-dimethoxy-2[4-(5-methylthio-1,3,4-oxadiazole-2-carbonyl]-piperazin-1-yl)-quinazoline wherein the base to acid ratio comprises one mole equivalent of said base to from 1.25 to 1.35 mole equivalents of said acid.

2. The salt of claim 1 having a base to acid ratio of one mole equivalent of 4-amino-6,7-dimethoxy-2-[4-(5-methylthio-1,3,4-oxadiazole-2-carbonyl]piperazin-1-yl)quinazoline and 1.3 mole equivalents of levulinic acid.

* * * * *